United States Patent
Brown

(10) Patent No.: US 9,022,962 B2
(45) Date of Patent: May 5, 2015

(54) APPARATUS FOR DETECTING AND TREATING VENTRICULAR ARRHYTHMIA

(75) Inventor: Ward M. Brown, Lacrosse, WI (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1833 days.

(21) Appl. No.: 10/968,889

(22) Filed: Oct. 21, 2004

(65) Prior Publication Data

US 2005/0143776 A1 Jun. 30, 2005

Related U.S. Application Data

(63) Continuation of application No. 10/460,300, filed on Jun. 13, 2003, now abandoned, which is a continuation of application No. 09/990,045, filed on Nov. 21, 2001, now abandoned.

(60) Provisional application No. 60/252,811, filed on Nov. 22, 2000.

(51) Int. Cl.
*A61N 1/362* (2006.01)
*A61N 1/39* (2006.01)
(Continued)

(52) U.S. Cl.
CPC ............ *A61N 1/3621* (2013.01); *A61N 1/0504* (2013.01); *A61N 1/36071* (2013.01); *A61N 1/3622* (2013.01); *A61N 1/3918* (2013.01); *A61N 1/3925* (2013.01); *A61N 1/3962* (2013.01); *A61N 1/362* (2013.01); *A61N 1/365* (2013.01); *A61N 1/3956* (2013.01)

(58) Field of Classification Search
CPC ..... A61N 1/39; A61N 1/3918; A61N 1/0504; A61N 1/3622
USPC ............................................................ 607/5
See application file for complete search history.

(56) References Cited

U.S. PATENT DOCUMENTS

| RE27,652 E | 5/1973 | Mirowski et al. |
| 4,030,509 A | 6/1977 | Heilman et al. |

(Continued)

FOREIGN PATENT DOCUMENTS

| EP | 0 347 353 A1 | 12/1989 |
| EP | 0 627 194 A2 | 12/1994 |

(Continued)

OTHER PUBLICATIONS

Communication mailed by the Japanese Patent Office on Sep. 5, 2006 for counterpart application No. 2002-544121 and English-language translation (12 pages).

(Continued)

*Primary Examiner* — George Evanisko
(74) *Attorney, Agent, or Firm* — Bookoff McAndrews, PLLC

(57) ABSTRACT

A system and method for long-term monitoring of cardiac conditions such as arrhythmias is disclosed. The invention includes a pulse generator including means for sensing an arrhythmia. The pulse generator is coupled to at least one subcutaneous electrode or electrode array for providing electrical stimulation such as cardioversion/defibrillation shocks and/or pacing pulses. The electrical stimulation may be provided between multiple subcutaneous electrodes, or between one or more such electrodes and the housing of the pulse generator. In one embodiment, the pulse generator includes one or more electrodes that are isolated from the can. These electrodes may be used to sense cardiac signals.

18 Claims, 9 Drawing Sheets

(51) Int. Cl.
*A61N 1/365* (2006.01)
*A61N 1/05* (2006.01)
*A61N 1/36* (2006.01)

(56) References Cited

U.S. PATENT DOCUMENTS

| | | | |
|---|---|---|---|
| 4,157,720 A | 6/1979 | Greatbatch |
| 4,164,946 A | 8/1979 | Langer |
| 4,184,493 A | 1/1980 | Langer et al. |
| 4,210,149 A | 7/1980 | Heilman et al. |
| RE30,372 E | 8/1980 | Mirowski et al. |
| RE30,387 E | 8/1980 | Denniston, III et al. |
| 4,223,678 A | 9/1980 | Langer et al. |
| 4,254,775 A | 3/1981 | Langer |
| 4,291,707 A | 9/1981 | Heilman et al. |
| 4,300,567 A | 11/1981 | Kolenik et al. |
| 4,310,000 A | 1/1982 | Lindemans |
| 4,375,817 A | 3/1983 | Engle et al. |
| 4,392,407 A | 7/1983 | LaFever et al. |
| 4,407,288 A | 10/1983 | Langer et al. |
| 4,408,607 A | 10/1983 | Maurer |
| 4,428,378 A | 1/1984 | Anderson et al. |
| 4,450,527 A | 5/1984 | Sramek |
| 4,548,209 A | 10/1985 | Wielders et al. |
| 4,567,900 A | 2/1986 | Moore |
| 4,595,009 A | 6/1986 | Leinders |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,768,512 A | 9/1988 | Imran |
| 4,821,723 A | 4/1989 | Baker, Jr. et al. |
| 4,830,005 A | 5/1989 | Woskow |
| 4,865,036 A | 9/1989 | Chirife |
| 4,932,407 A | 6/1990 | Williams |
| 4,944,300 A | 7/1990 | Saksena |
| 4,958,632 A | 9/1990 | Duggan |
| 4,967,747 A | 11/1990 | Carroll et al. |
| 5,005,587 A * | 4/1991 | Scott .................... 607/122 |
| 5,044,374 A | 9/1991 | Lindemans et al. |
| 5,083,562 A * | 1/1992 | de Coriolis et al. ............... 607/7 |
| 5,105,810 A | 4/1992 | Collins et al. |
| 5,105,826 A | 4/1992 | Smits et al. |
| 5,119,832 A | 6/1992 | Xavier |
| 5,129,392 A | 7/1992 | Bardy et al. |
| 5,133,353 A | 7/1992 | Hauser |
| 5,158,078 A | 10/1992 | Bennett et al. |
| 5,170,784 A | 12/1992 | Ramon et al. |
| 5,176,137 A | 1/1993 | Erickson et al. |
| 5,181,511 A * | 1/1993 | Nickolls et al. ................ 607/14 |
| 5,184,616 A | 2/1993 | Weiss |
| 5,193,535 A | 3/1993 | Bardy et al. |
| 5,193,536 A | 3/1993 | Mehra |
| 5,203,348 A | 4/1993 | Dahl et al. |
| 5,205,286 A | 4/1993 | Soukup et al. |
| 5,209,229 A | 5/1993 | Gilli |
| 5,215,081 A | 6/1993 | Ostroff |
| 5,224,475 A | 7/1993 | Berg et al. |
| 5,230,337 A | 7/1993 | Dahl et al. |
| 5,243,978 A | 9/1993 | Duffin, Jr. |
| 5,251,624 A | 10/1993 | Bocek et al. |
| 5,255,691 A | 10/1993 | Otten |
| 5,255,692 A | 10/1993 | Neubauer et al. |
| 5,261,400 A | 11/1993 | Bardy |
| 5,292,338 A | 3/1994 | Bardy |
| 5,300,106 A | 4/1994 | Dahl et al. |
| 5,313,953 A | 5/1994 | Yomtov et al. |
| 5,314,430 A | 5/1994 | Bardy |
| 5,318,593 A | 6/1994 | Duggan |
| 5,330,505 A | 7/1994 | Cohen |
| 5,331,966 A | 7/1994 | Bennett et al. |
| 5,342,407 A | 8/1994 | Dahl et al. |
| 5,354,316 A | 10/1994 | Keimel |
| 5,360,441 A | 11/1994 | Otten |
| 5,360,442 A * | 11/1994 | Dahl et al. ................ 607/129 |
| 5,366,485 A | 11/1994 | Kroll et al. |
| 5,366,496 A | 11/1994 | Dahl et al. |
| 5,376,103 A | 12/1994 | Anderson et al. |
| 5,376,105 A | 12/1994 | Hedberg |
| 5,385,574 A | 1/1995 | Hauser et al. |
| 5,405,363 A | 4/1995 | Kroll et al. |
| 5,411,539 A | 5/1995 | Neisz |
| 5,411,547 A | 5/1995 | Causey, III |
| 5,423,326 A | 6/1995 | Wang et al. |
| 5,433,730 A | 7/1995 | Alt |
| 5,439,484 A | 8/1995 | Mehra |
| 5,439,485 A | 8/1995 | Mar et al. |
| 5,447,521 A | 9/1995 | Anderson et al. |
| 5,458,619 A | 10/1995 | Olson |
| 5,466,254 A | 11/1995 | Helland |
| 5,470,341 A | 11/1995 | Kuehn et al. |
| 5,476,503 A | 12/1995 | Yang |
| 5,531,766 A | 7/1996 | Kroll et al. |
| 5,534,019 A | 7/1996 | Paspa |
| 5,534,022 A | 7/1996 | Hoffmann et al. |
| 5,545,202 A | 8/1996 | Dahl et al. |
| 5,601,607 A | 2/1997 | Adams |
| 5,603,732 A | 2/1997 | Dahl et al. |
| 5,607,455 A | 3/1997 | Armstrong |
| 5,609,621 A | 3/1997 | Bonner |
| 5,618,287 A | 4/1997 | Fogarty |
| 5,620,477 A | 4/1997 | Pless et al. |
| 5,645,586 A | 7/1997 | Meltzer |
| 5,658,319 A | 8/1997 | Kroll |
| 5,658,321 A | 8/1997 | Fayram |
| 5,662,688 A | 9/1997 | Haefner et al. |
| 5,701,895 A | 12/1997 | Prutchi et al. |
| 5,713,926 A | 2/1998 | Hauser et al. |
| 5,730,142 A | 3/1998 | Sun et al. |
| 5,733,313 A | 3/1998 | Barreras, Sr. et al. |
| 5,738,105 A | 4/1998 | Kroll |
| 5,766,226 A | 6/1998 | Pedersen |
| 5,792,205 A | 8/1998 | Alt et al. |
| 5,827,326 A | 10/1998 | Kroll et al. |
| 5,843,132 A | 12/1998 | Ilvento |
| 5,849,031 A | 12/1998 | Martinez et al. |
| 5,855,593 A | 1/1999 | Olson et al. |
| 5,893,881 A | 4/1999 | Elsberry et al. |
| 5,895,414 A | 4/1999 | Sanchez-Zambrano |
| 5,904,705 A | 5/1999 | Kroll et al. |
| 5,916,238 A * | 6/1999 | Hauser et al. ................ 607/5 |
| 5,957,956 A | 9/1999 | Kroll et al. |
| 6,058,328 A | 5/2000 | Levine et al. |
| 6,091,989 A | 7/2000 | Swerdlow et al. |
| 6,093,173 A | 7/2000 | Balceta et al. |
| 6,095,987 A | 8/2000 | Shmulewitz |
| 6,144,879 A | 11/2000 | Gray |
| 6,148,230 A | 11/2000 | KenKnight |
| 6,157,860 A | 12/2000 | Hauser et al. |
| 6,167,308 A | 12/2000 | DeGroot |
| 6,178,350 B1 | 1/2001 | Olson et al. |
| 6,212,063 B1 | 4/2001 | Johnson et al. |
| 6,230,059 B1 | 5/2001 | Duffin |
| 6,266,567 B1 | 7/2001 | Ishikawa et al. |
| 6,272,379 B1 * | 8/2001 | Fischell et al. ................ 607/5 |
| 6,278,894 B1 | 8/2001 | Salo et al. |
| 6,280,462 B1 | 8/2001 | Hauser et al. |
| 6,295,474 B1 | 9/2001 | Munshi |
| 6,334,071 B1 | 12/2001 | Lu |
| 6,345,198 B1 | 2/2002 | Mouchawar et al. |
| 6,436,068 B1 | 8/2002 | Bardy |
| 6,505,067 B1 | 1/2003 | Lee et al. |
| 6,640,135 B1 | 10/2003 | Salo et al. |
| 6,647,292 B1 | 11/2003 | Bardy et al. |
| 6,718,628 B2 | 4/2004 | Munshi |
| 6,721,597 B1 | 4/2004 | Bardy et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,927,721 B2 | 8/2005 | Ostroff |

(56) References Cited

U.S. PATENT DOCUMENTS

| | | |
|---|---|---|
| 6,937,907 B2 | 8/2005 | Bardy et al. |
| 6,950,705 B2 | 9/2005 | Bardy et al. |
| 6,952,608 B2 | 10/2005 | Ostroff |
| 6,952,610 B2 | 10/2005 | Ostroff et al. |
| 6,954,670 B2 | 10/2005 | Ostroff |
| 6,988,003 B2 | 1/2006 | Bardy et al. |
| 6,999,814 B2 | 2/2006 | Hauser et al. |
| 7,292,887 B2 | 11/2007 | Salo et al. |
| 7,330,757 B2 | 2/2008 | Ostroff |
| 7,522,959 B2 | 4/2009 | Hauser |
| 2001/0037134 A1 | 11/2001 | Munshi |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0188252 A1 | 12/2002 | Bardy |
| 2002/0193834 A1* | 12/2002 | Levine ................... 607/9 |
| 2003/0036778 A1 | 2/2003 | Ostroff et al. |
| 2003/0045904 A1 | 3/2003 | Bardy et al. |
| 2003/0088277 A1 | 5/2003 | Ostroff |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0212436 A1 | 11/2003 | Brown |
| 2004/0064177 A1 | 4/2004 | Bardy et al. |
| 2005/0021093 A1 | 1/2005 | Brown |
| 2005/0038476 A1 | 2/2005 | Brown |
| 2005/0119707 A1 | 6/2005 | Hauser et al. |
| 2005/0131464 A1 | 6/2005 | Heinrich et al. |
| 2005/0143776 A1 | 6/2005 | Brown |
| 2006/0015163 A1 | 1/2006 | Brown |
| 2006/0142804 A1 | 6/2006 | Hauser et al. |
| 2008/0140139 A1 | 6/2008 | Heinrich et al. |

FOREIGN PATENT DOCUMENTS

| | | |
|---|---|---|
| EP | 0 627 237 A1 | 12/1994 |
| EP | 0 460 324 B1 | 3/1996 |
| EP | 0 578 748 B1 | 5/1996 |
| EP | 0 517 494 B1 | 9/1996 |
| EP | 1 318 855 B1 | 9/2001 |
| JP | 64-76877 | 3/1989 |
| JP | 4-40966 | 2/1992 |
| JP | 5-64666 | 3/1993 |
| JP | 5-67310 | 9/1993 |
| JP | 6-47098 | 2/1994 |
| JP | 6-505662 | 6/1994 |
| JP | 07-000538 | 1/1995 |
| JP | 7-148275 | 6/1995 |
| JP | 2655204 | 5/1997 |
| WO | WO 92/17240 | 10/1992 |
| WO | WO 92/20402 | 11/1992 |
| WO | WO 94/03233 | 2/1994 |
| WO | WO 95/09030 | 4/1995 |
| WO | WO 97/29802 A3 | 8/1997 |
| WO | WO 99/38568 | 8/1999 |
| WO | WO 99/53991 A1 | 10/1999 |
| WO | WO 00/07497 | 2/2000 |
| WO | WO 00/41765 | 7/2000 |
| WO | WO 02/22208 | 3/2002 |
| WO | WO 02/24275 | 3/2002 |

OTHER PUBLICATIONS

Berul et al., "Minimally Invasive Cardioverter Defibrillator Implantation for Children: An Animal Model and Pediatric Case Report," Pacing and Clinical Electrophysiology, vol. 24, Issue 12, pp. 1789-1799, Dec. 2001.

Böcker et al., "Treatment with Implantable Defibrillators in Childhood," Herzschr Elektrophys, 10(4), pp. 248-251 (Dec. 1999).

Gradaus et al., "Nonthoracotomy Implantable Cardioverter Defibrillator Placement in Children: Use of Subcutaneous Array Leads and Abdominally Placed Implantable Cardioverter Defibrillators in Children," Journal of Cardiovascular Electrophysiology, vol. 12, No. 3, pp, 356-360, Mar. 2001.

Hoffmann et al., "Experience Wth Pectoral Versus Abdominal Implantation of a Small Defibrillator," European Heart Journal, vol. 19, pp. 1085-1098, 1998.

International Preliminary Examination Report issued in PCT/US01/43513, Jan. 2003.

International Search Report issued in PCT/US01/43513, Sep. 2002.

Leng et al., "Lead Configuration for Defibrillator Implantation in a Patient with Cogenital Heart Disease and a Mechanical Prosthetic Tricuspid Valve," PACE vol. 24, No. 8, pp. 1921-1292, Aug. 2001.

Office Action dated Oct. 15, 2004, issued in European Application No. 01 987 042.7-1265.

Park et al., "Use of an Implantable Cardioverter Defibrillator in an Eight-Month-Old Infant with Ventricular Fibrillation Arising from a Myocardial Fibroma," PACE vol. 22, No. 1, Part I, pp. 138-139, Jan. 1999.

European Search Report in European Application No. EP 05105683, issued Aug. 2005.

Schuder et al., "Experimental Ventricular Defibrillation with an Automatic and Completely Implanted System," Trans. Amer. Soc. Artif. Int. Organs, vol. XVI, pp. 207-212, 1970.

Schuder et al., "Ventricular Defibrillation in the Dog Using Implanted and Partially Implanted Electrode Systems," The American Journal of Cardiology, vol. 33, pp. 243-247, Feb. 1974.

Stirbis et al., "Optimizing the Shape of Implanted Artifical Pacemakers," Biomedical Engineering vol. 20, No. 6, pp. 199-200, Nov.-Dec. 1986 and Jul. 1987.

Subcutaneous Lead System, Model 6996SQ, http://www.medtronic.com/tachy2/leads/6996sq.html, Feb. 7, 2005.

Written Opinion issued in PCT/US01/43513, Sep. 2002.

Communication mailed by the European Patent Office on Feb. 7, 2007 for counterpart European Application No. 06126700.1 (10 pages).

International Search Report dated Mar. 26, 2002, issued in PCT/US01/29168 filed Sep. 14, 2001, published as WO 02/22208 on Mar. 21, 2002, Subcutaneous Only Implantable Cardioverter Defibrillator & Optional Pacer, Inventors: Gust H. Bardy et al.

International Search Report dated Mar. 21, 2002, issued in PCT/US01/29106 filed Sep. 14, 2001, published as WO 02/24275 on Mar. 28, 2002, Unitary Subcutaneous Only Implantable Cardioverter Defibrillator & Optical Pacer, Inventors: Gust H. Bardy et al.

J.C. Schuder, PhD., an editorial comment, "Completely Implanted Defibrallator," Journal of the American Medical Association (JAMA), vol. 214, No. 6, p. 1123, Nov. 9, 1970.

J.C. Schuder, PhD., an editorial comment, "Standby Implanted Defibrillators," Archives of Internal Medicine (Specialized Journal of the AMA), vol. 127, Letters to the Editor, p. 317, Feb. 1971.

(56) References Cited

OTHER PUBLICATIONS

Mirkowski et al., "Automatic Detection & Fibrillation of Lethal Arrythmias—A New Concept," Journal of the American Medical Association (JAMA), vol. 213, pp. 615-616, 1970.
J.C. Schuder, PhD., et al., "Transthoracic Ventriculator Defibrillation in the Dog With Truncated and Untruncated Exponential Stimuli," IEEE Transactions on Bio-Medical Engineering, vol. BME-18, No. 6, pp. 410-145, Nov. 1971.
J.C. Schuder, PhD., "The Role of an Engineering Oriented Medical Research Group in Developing Improved Methods & Devices for Achieving Ventricular Defibrillation: The University of Missouri Experience," PACE, vol. 16, Part I, pp. 95-124, Jan. 1993.
Richard A. Friedman, M.D., et al., "Implantable Defibrillators in Children: From Whence to Shock," Journal of Cardiovascular Electrophysiology, vol. 12, No. 3, pp. 361-362, Mar. 2001, Copyright 2001, by Future Publishing Company Inc., Armonk—NY 1050-0418.
Valenzuela et al., "Outcomes of Rapid Defibrillation by Security Officers After Cardiac Arrest in Casinos", NEJM, vol. 343, No. 17, pp. 1206-1209, Oct. 26, 2000.
Higgins et al, "The First Year Experience with the Dual Chamber ICD," PACE 23, pp. 18-25, Jan. 2000.
Bardy et al., "Multicenter Experience with a Pectoral Unipolar Implantable Cardioverter-Defibrillator," JACC, vol. 28, No. 1, pp. 400-410, Aug. 1996.
Olson et al., "Onset and Stability for Ventricular Tachyarrhythmia Detection in an Implantable Cardioverter and Defibrallator," Computers in Cardiology, pp. 167-170, 1986.
Communication by the Japanese Patent Office dated Apr. 11, 2007 from counterpart application No. 2002-544121 and English-language translation (8 pages).
Communication mailed by the European Patent Office on Jun. 19, 2006 for European Application No. 05105683.6.
Office Action dated Oct. 7, 2009, issued in Canadian Application No. 2,428,873 (3 pgs).
"The Essential Tool for Patients at Increased Risk for Arrhythmias," Reveal Plus Insertable Loop Recorder (ILR), Model 9526, 6 pages, © 2001 Medtronic.
Schwacke et al., "Komplikationen mit Sonden bei 340 Patienten mit einem implantierbaren Kardioverter/Defibrillator," Z Kardiol 88, pp. 559-565, Aug. 1999.
Communication mailed by the European Patent Office on Oct. 1, 2007 for counterpart European Application No. 08126700.1 (12 pages).
Subcutaneous Lead System, Model 6996SQ http://www.medtronic.com/tachy/clinician/leads/spec6996sq.html, Oct. 2, 2002.
Official Action mailed on Apr. 13, 2010, in corresponding Japanese Application No. 2007-211759.
English Language Transcript of Decision of Final Rejection mailed on Nov. 9, 2010, in corresponding Japanese Application No. 2007-211759.
Communication pursuant to Article 94(3) EPC dated Jun. 15, 2010, in corresponding European Application No. 06 126 700.1.
Communication under Rule 71(3) EPC dated Nov. 19, 2010 in corresponding European Application No. 06 126 700.1.
Office Action (Election/Restriction Requirement) mailed on Sep. 18, 2008, in co-pending U.S. Appl. No. 10/949,877.
Response to Sep. 18, 2008, Office Action (Election/Restriction Requirement) filed on Mar. 18, 2009, in co-pending U.S. Appl. No. 10/949,877.
Office Action mailed on Apr. 20, 2009, in co-pending U.S. Appl. No. 10/949,877.
Response to Apr. 20, 2009, Office Action filed on Oct. 19, 2009, in co-pending U.S. Appl. No. 10/949,877.
Final Office Action mailed on Jan. 4. 2010, in co-pending U.S. Appl. No. 10/949,877.
Response to Jan. 4, 2010 final Office Action filed on Feb. 1, 2011, in co-pending U.S. Appl. No. 10/949,877.
Response to Jun. 15, 2010 Communication filed on Oct. 19, 2010, in corresponding European Application No. 06 126 700.1.
Response to Oct. 7, 2009 Office Action filed on Apr. 7, 2010, in corresponding Canadian Application No. 2,428,873.
Office Action (Election/Restriction Requirement) mailed on Dec. 17, 2009, in co-pending U.S. Appl. No. 11/981,410.
Response to Dec. 17, 2009, Office Action (Election/Restriction Requirement) filed on Jun. 16, 2010, in co-pending U.S. Appl. No. 11/981,410.
Office Action mailed on Aug. 23, 2010, in co-pending U.S. Appl. No. 11/981,410.
Response to Aug. 23, 2010, Office Action filed on Feb. 22, 2011, in co-pending U.S. Appl. No. 11/981,410.
Summons to attend oral proceedings pursuant to Rule 115(1) EPC for European Patent Application No. 01973151.2-1657/1318856, dated Oct. 11, 2013, 6 pages.
Response to Communication dated Oct. 1, 2007, from European patent application No. 06126700.1-1265, filed Apr. 11, 2008, 27 pages.
Office Action dated Jun. 19, 2014, from U.S. Appl. No. 13/476,940, filed May 21, 2012, 21 pages.
Office Action dated Jul. 15, 2014, from U.S. Appl. No. 14/275,845, filed May 12, 2014, 10 pages.

* cited by examiner

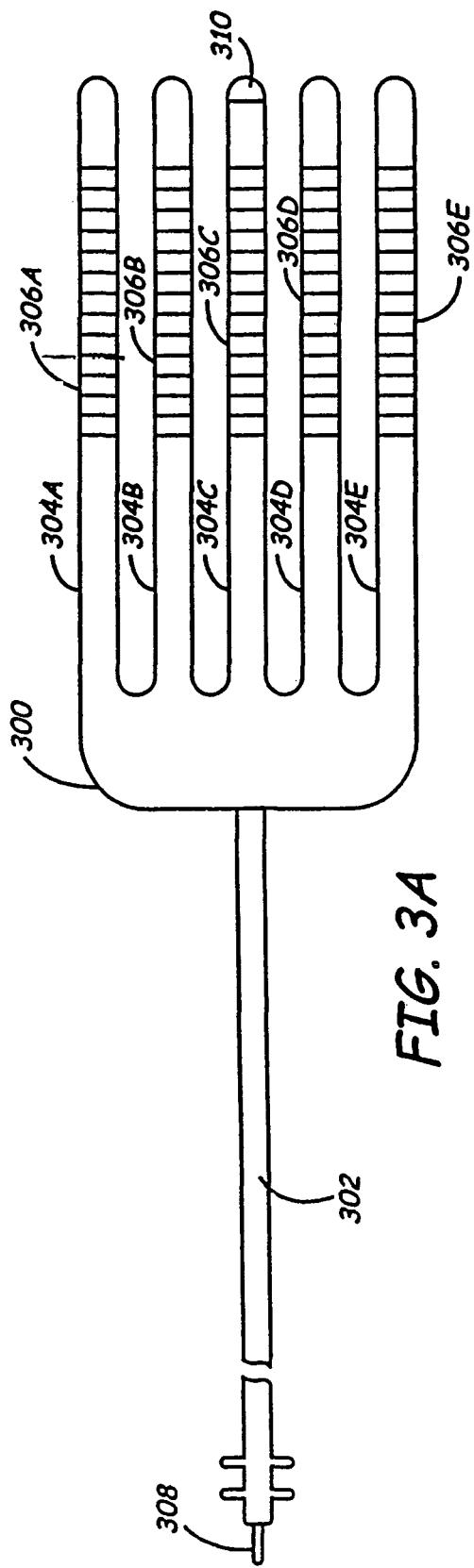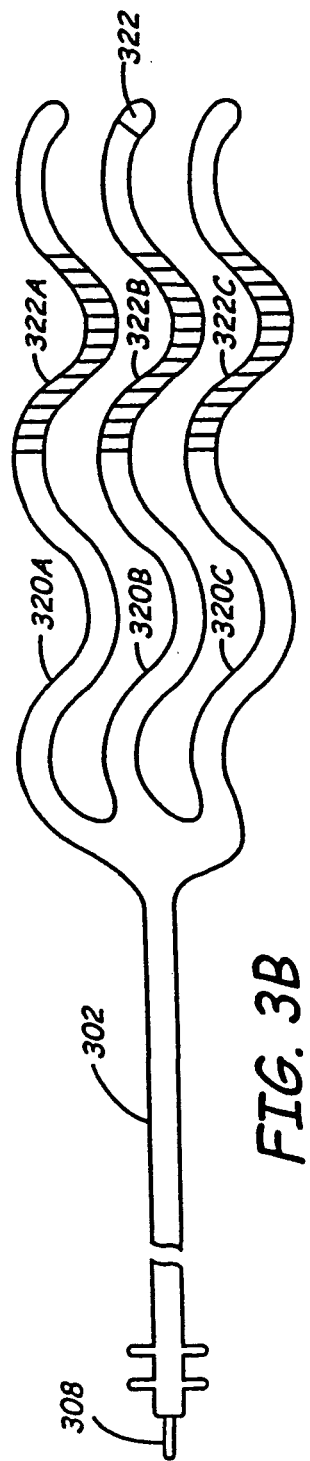

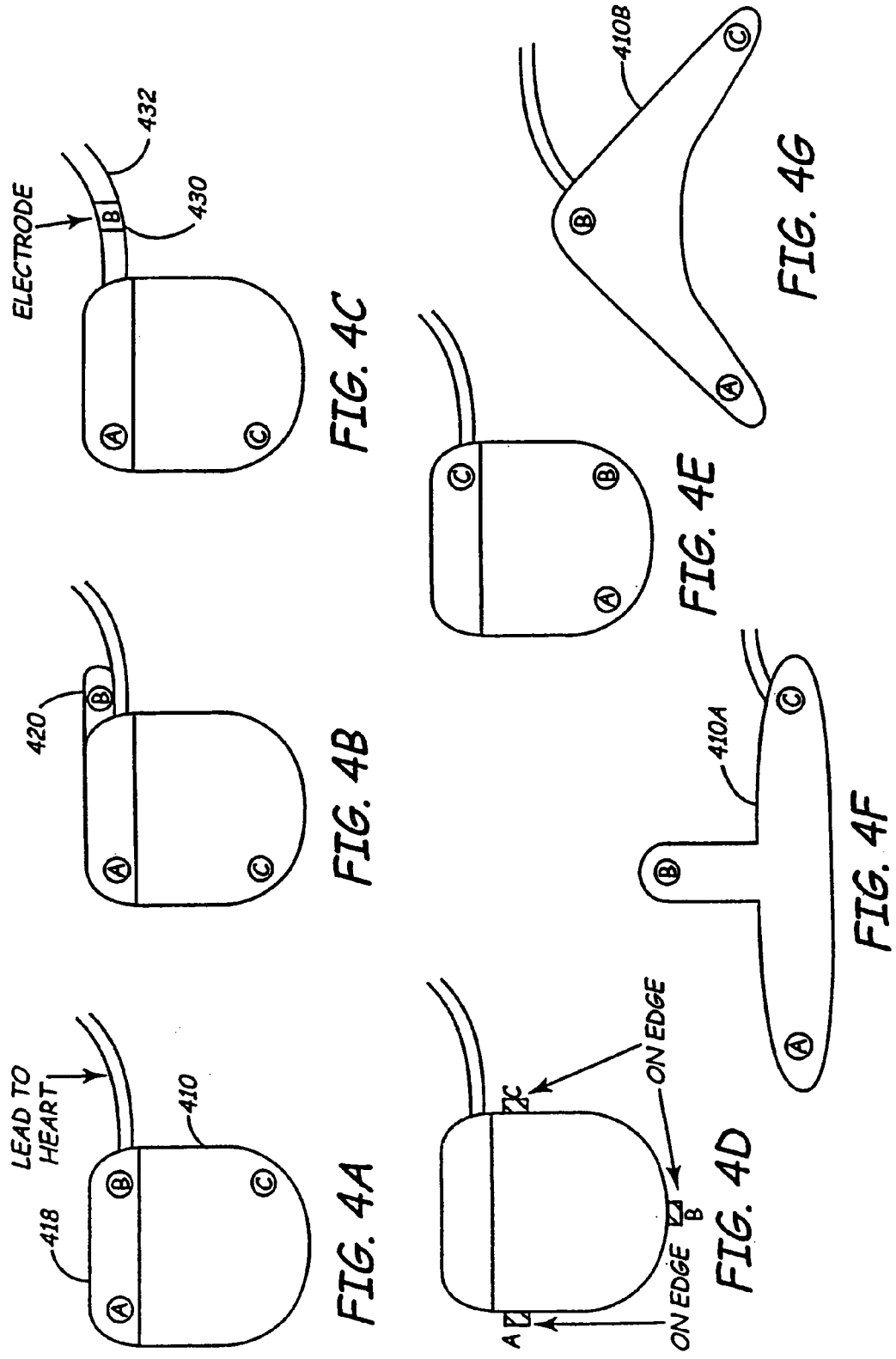

APPARATUS FOR DETECTING AND TREATING VENTRICULAR ARRHYTHMIA

This is a continuation of application Ser. No. 10/460,300, filed Jun. 13, 2003 now abandoned, which is a continuation of application Ser. No. 09/990,045, filed Nov. 21, 2001 now abandoned, which claims the benefit of U.S. Provisional Application No. 60/252,811, filed Nov. 22, 2000, all of which are incorporated herein by reference.

FIELD OF THE INVENTION

This invention relates to a method and apparatus for treating ventricular arrhythmias; and more particularly, relates to a method and apparatus for long-term monitoring of arrhythmias, and for the delivery of acute tachyarrhythmia and bradyarrhythmia therapy using a subcutaneous stimulation device.

DESCRIPTION OF THE PRIOR ART

It has long been known to use implantable systems to protect patients that are at risk for life-threatening arrhythmias. For example, rapid heart rhythms commonly referred to as tachyarrhythmias are generally treated using implantable devices such as the Medtronic Model 7273 GEM II DR or the 7229 GEM II SR, both commercially available from the Medtronic Corporation. These systems detect the presence of tachyarrhythmia conditions by monitoring the electrical and mechanical heart activity (such as intra-myocardial pressure, blood pressure, impedance, stroke volume or heart movement) and/or the rate of the electrocardiogram. These devices require that one or more defibrillation electrodes be positioned within the atrium and/or ventricle of a patient's heart using current endocardial lead placement techniques. The use of such systems provides consistent long-term monitoring capabilities, and relatively good protection against life-threatening tachyarrhythmias.

Similarly, bradyarrhythmias, which are heart rhythms that are too slow, are generally treated using implantable pulse generators. Such devices are described in U.S. Pat. Nos. 5,158,078, 4,958,632, and 5,318,593, for example. As with devices to treat tachyarrhythmias, most implantable pulse generators that treat these types of conditions generally require leads that are implanted within one or more cardiac chambers.

Although the use of endocardial leads placed within the cardiac chambers of a patient's heart provides the capability to deliver a relatively reliable, long-term arrhythmia therapy, there are disadvantages associated with such treatments. The placement of these leads requires a relatively time-consuming, costly procedure that is not without risks to the patient including infection, the possibility of vascular perforation, and tamponade.

Moreover, some people are not candidates for endocardial leads. For example, patients with artificial mechanical tricuspid valves are generally not candidates for leads that extend from the night atrium, through this valve, to the right ventricle, as is the case with most right ventricular endocardial leads. This is because the use of such leads interfere with the proper mechanical functioning of the valves. Other patients that are not candidates for endocardial lead placement include those with occluded venous access, or patients with congenital heart defects.

Patients that are contraindicated for endocardial lead placement must often undergo a procedure to attach the lead to the external surface of the heart. This type of epicardial lead placement involves a more invasive procedure that requires a longer recovery time, makes follow-up procedures very difficult, and is also associated with increased patient risk, including an increased chance of contracting an infection.

Another problem associated with both endocardial and epicardial leads involves patient growth. More specifically, a lead placed within a child's cardiac vasculature will likely need to be re-positioned or replaced as the child matures. Such lead replacement procedures can be dangerous, especially when previously-placed leads are extracted rather than left in position within the body.

One alternative to endocardial and epicardial leads involves subcutaneously-placed electrode systems. For example, in U.S. Pat. No. RE30,372 by Mirowski, et al., a defibrillation system employs a ventricular endocardial electrode and a plate electrode mounted to the heart directly, subcutaneously, or to the skin to deliver high voltage therapy to the patient. A similar lead system disclosed in U.S. Pat. No. 5,314,430 to Bardy includes a coronary sinus/great vein electrode and a subcutaneous plate electrode located in the left pectoral region which may optionally take the form of a surface of the defibrillator housing.

What is needed, therefore, is a system and method that can provide long-term monitoring for various types of arrhythmias, provide patient therapy when needed, and also overcome the problems associated with both endocardial and epicardial lead placement.

SUMMARY OF THE INVENTION

The current invention provides a system and method for long-term monitoring for arrhythmias. The invention includes a pulse generator including means for sensing an arrhythmia. The pulse generator is coupled to at least one electrode or electrode array for providing electrical stimulation to a patient. The stimulation may include cardioversion/defibrillation shocks and/or pacing pulses. The electrical stimulation may be provided between multiple electrodes, or between one or more electrodes and the housing of the pulse generator. In one embodiment, the pulse generator includes one or more electrodes that are isolated from the can. These electrodes may be used to sense cardiac signals.

According to one embodiment of the invention, an apparatus is provided for monitoring cardiac signals of a patient. The apparatus includes a hermetically-sealed housing, sensing means included within the housing, and first and second electrode sets coupled to the sensing means. The first electrode set includes at least one electrode adjacent to a surface of the housing positionable proximate subcutaneous tissue at a first location in the patient's body. The second electrode set is coupled to a connector on the housing and forms an electrode array subcutaneously-positionable in the patient's body at a location different from the first location.

According to another embodiment of the invention, a method of therapy is provided. This method includes monitoring the patient's cardiac signals for a condition such as an arrhythmia, and hereafter delivering a electrical therapy to a patient via a subcutaneous electrode array is the condition is detected. Other aspects of the invention will become apparent from the drawings and the accompanying description.

BRIEF DESCRIPTION OF THE DRAWINGS

FIG. 3 is a top view of an electrode array 300 as may be used with the current invention.

FIG. 4A is a side view of a pulse generator illustrating the orientation of electrodes A, B and C disposed on the device housing.

FIG. 4B is a side view of a pulse generator wherein at least one of the electrodes extends away from the pulse generator via a lead extension.

FIG. 4C is a side view of a pulse generator wherein at least one of the electrodes is located at a proximal end of a lead.

FIG. 4D is a side view of a pulse generator wherein multiple electrodes are located on an edge of a device housing.

FIG. 4E is a side view of yet another embodiment of a device housing including an array of electrodes.

FIG. 4F is a side view of a device having a first alternative shape.

FIG. 4G is a side view of a device having a second alternative shape.

DETAILED DESCRIPTION OF THE PREFERRED EMBODIMENTS

The current invention provides a system and method for long-term monitoring for arrhythmias. The invention also provides acute therapy delivery in the event an arrhythmia episode is detected. According to one embodiment of the invention, a subcutaneous pulse generator is provided. This pulse generator may be a transthoracic Implantable Cardioversion/Defibrillator (ICD) such as the GemDR™ Model 7271 or the GEM II VR Model 7229, both commercially available from the Medtronic Corporation. The pulse generator is coupled to at least one subcutaneously-placed electrode or electrode array. Cardioversion/defibrillation pulses and/or pacing pulses may be delivered between the electrode and the can of the device, or between two subcutaneously-placed electrodes.

Figure 1:
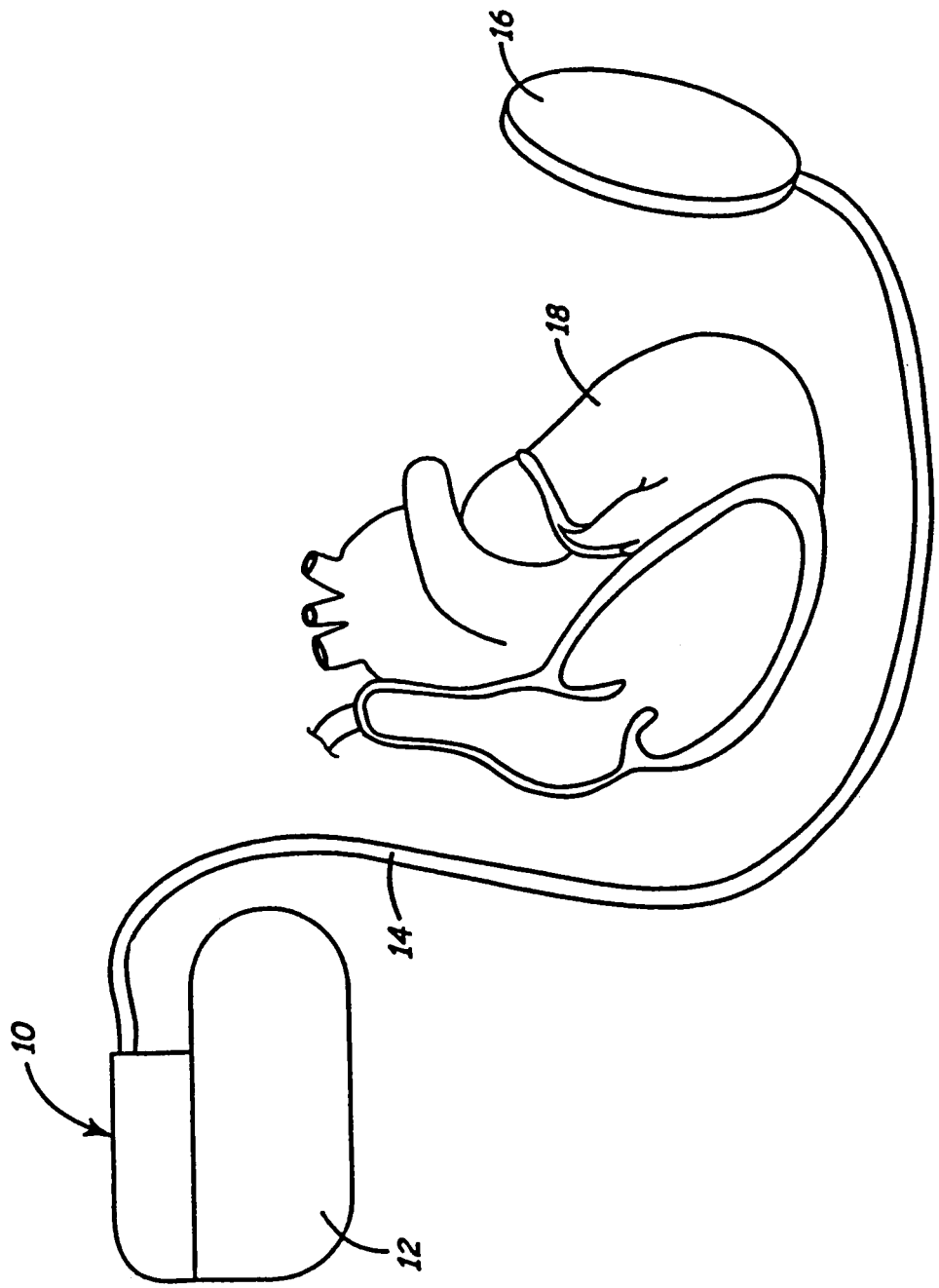
FIG. 1 illustrates an exemplary subcutaneous electrode and pulse generator as may be used in accordance with the current invention.

FIG. 1 illustrates an implantable pulse generator 10 and an exemplary associated lead system according to the current invention. Pulse generator 10 includes a device housing 12, and is further coupled to a lead 14 which may be implanted subcutaneously in the left chest or on the back as discussed below. Lead 14 may include a subcutaneous plate electrode 16, which may be any of the various known subcutaneous plate electrodes. This type of subcutaneous electrode may be located proximal the left ventricular-cavity on the patient's chest, on the patient's side or back, or any other portion of the body appropriate for providing electrical stimulation to the heart. Similar electrodes are disclosed in U.S. Pat. Nos. 4,392, 407, 5,261,400, and 5,292,338, all incorporated herein by reference. During use, electrical stimulation may be delivered to heart 18 between electrode 16 and device housing 12.

Figure 2:
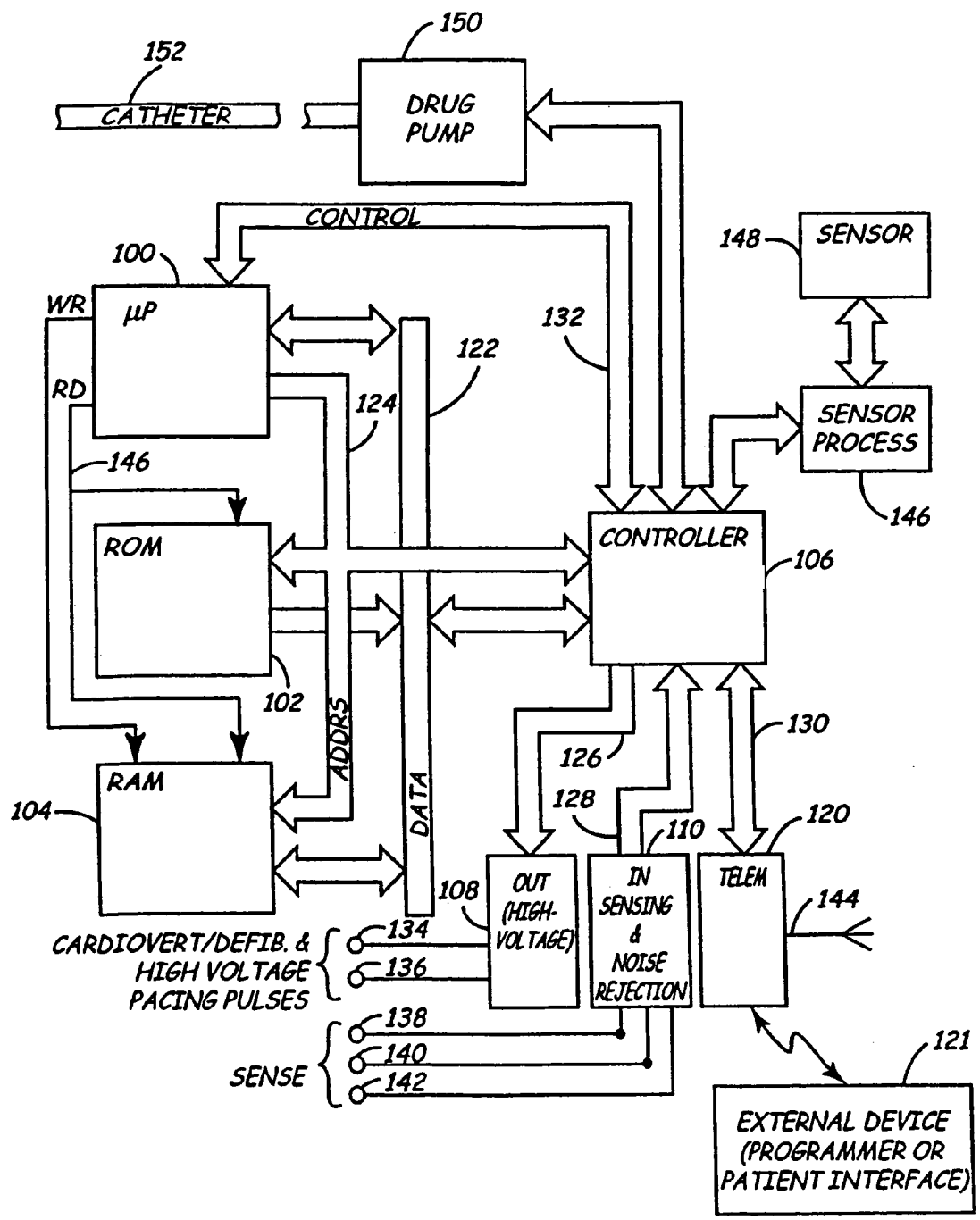
FIG. 2 is a block functional diagram of an illustrative embodiment of a pulse generator that maybe employed according to the present invention.

FIG. 2 is a block functional diagram of an illustrative embodiment of a pulse generator that may be employed according to the present invention. As illustrated, the device is embodied as a microprocessor-based stimulator. However, other digital circuitry embodiments and analog circuitry embodiments are also believed to be within the scope of the invention. For example, devices having general structures as illustrated in U.S. Pat. No. 5,21,624 issued to Bocek et al., U.S. Pat. No. 5,209,229 issued to Gilli, U.S. Pat. No. 4,407, 288, issued to Langer et al, U.S. Pat. No. 5,662,688, issued to Haefner et al., U.S. Pat. No. 5,855,893, issued to Olson et al., U.S. Pat. No. 4,821,723, issued to Baker et al. or U.S. Pat. No. 4,967,747, issued to Carroll et al., all incorporated herein by reference in their entireties, may also be usefully employed in conjunction with the present invention. FIG. 1 should thus be considered illustrative, rather than limiting with regard to the scope of the invention.

The primary elements of the apparatus illustrated in FIG. 2 are a microprocessor 100, read-only memory (ROM) 102, random-access memory (RAM) 104, a digital controller 106, an input amplifier circuit 110, two output circuits 108 and 109, and a telemetry/programming unit 120. Read-only memory stores software and/or firmware for the device, including the primary instruction set defining the computations performed to derive the various timing intervals employed by the device. RAM 104 generally serves to store variable control parameters, such as programmed pacing rate, programmed cardioversion/defibrillation intervals, pulse widths, pulse amplitudes, and so forth which are programmed into the device by the physician. Random-access memory 104 also stores derived values, such as the stored time intervals separating tachyarrhythmia pulses and the corresponding high-rate pacing interval.

Controller 106 performs all of the basic control and timing functions of the device. Controller 106 includes at least one programmable timing counter, which is used to measure timing intervals within the context of the current invention. On time out of the pacing escape interval or in response to a determination that a cardioversion, defibrillation, or pacing pulse is to be delivered, controller 106 triggers the appropriate output pulse from high-voltage output stage 108, as discussed below. In one embodiment, controller may also control the amplitude of pacing pulses, as well as the energy associated with defibrillation and cardioversion shocks.

Following generation of stimulus pulses, controller 106 may be utilized to generate corresponding interrupts on control lines 132 to microprocessor 100, allowing it to perform any required mathematical calculations, including all operations associated with evaluation of return cycle times and selection of anti-tachyarrhythmia therapies according to the present invention. The timing/counter circuit in controller 106 also may control timing intervals such as ventricular refractory periods, as is known in the art. The time intervals may be determined by programmable values stored in RAM 104, or values stored in ROM.

Controller 106 may also generate interrupts for microprocessor 100 on the occurrence of sensed ventricular depolarizations or beats. The timing and morphology of sensed cardiac waveforms may also be used by microprocessor 100 to determine whether an arrhythmia is occurring so that therapy may be delivered as discussed further below.

Output stage 108 contains a high-output pulse generator capable of generating cardioversion/defibrillation pulses. According to the current invention, these pulses may be applied between a subcutaneous electrode or electrode array coupled to terminal 134 and the can of the pulse generator. Alternatively, the pulses may be provided between an electrode coupled to terminal 134 and a second subcutaneous electrode or electrode array coupled to terminal 136. Typically the high-output pulse generator includes one or more high-voltage capacitors, a charging circuit, and a set of switches to allow delivery of monophasic or biphasic cardioversion or defibrillation pulses to the electrodes employed. Output circuit 108 may further provide pacing pulses to the heart under the control of controller 106. These pacing pulses, which may be between 0 and 10 volts in amplitude, are provided via one or more of the subcutaneously-located electrodes.

Sensing of ventricular depolarizations (beats) is accomplished by input circuit 110, which is coupled to electrode 138 and one of electrodes 140 and 142. This circuitry may include amplification, and noise detection and protection circuitry. In one embodiment, signal sensing is disabled during periods of excessive noise. Noise rejection filters and similar circuitry may also be included, as is known in the art. Input circuit 110 provides signals indicating both the occurrence of natural ventricular beats and paced ventricular beats to the controller 106 via signal lines 128. Controller 106 provides signals indicative of the occurrence of such ventricular beats to microprocessor 100 via signal lines 132, which may be in the form of interrupts. This allows the microprocessor to perform any necessary calculations or to update values stored in RAM 104.

Optionally included in the device may be one or more subcutaneously or cutaneously-positioned physiologic sensors 148, which may be any of the various known sensors for use in conjunction with implantable stimulators. Any sensor of this type known in the art may be employed within the context of the current invention. Additionally, if desired, sensors positioned within the cardiovascular system may be utilized. For example, sensor 148 may be a hemodynamic sensor such as an impedance sensor as disclosed in U.S. Pat. No. 4,86,036, issued to Chirife or a pressure sensor as disclosed in U.S. Pat. No. 5,330,505, issued to Cohen, both of which are incorporated herein by reference in their entireties. Alternatively, sensor 148 may be a demand sensor for measuring cardiac output parameters, such as an oxygen saturation sensor disclosed in U.S. Pat. No. 5,176,137, issued to Erickson et al. or a physical activity sensor as disclosed in U.S. Pat. No. 4,428,378, issued to Anderson et al., both of which are incorporated herein by reference in their entireties.

Sensor processing circuitry 146 transforms the sensor output into digitized values for use in conjunction with detection and treatment of arrhythmias. These digitized signals may be monitored by controller 106 and microprocessor 100 and used alone or in combination with sensed electrical cardiac signals to provide diagnostic information used to determine the onset of an arrhythmia or other cardiac conditions. These signals may also be used to determine an optimal time for shock delivery. For example, an impedance sensor may be used to determine when a patient has exhaled so that shock delivery may occur when the lungs are relatively deflated, since this may result in lower defibrillation thresholds (DFTs). Sensor signals may also be stored in RAM 104 for later diagnostic use.

External control of the implanted cardioverter/defibrillator is accomplished via telemetry/control block 120 that controls communication between the implanted cardioverter/pacemaker and an external device 121. Any conventional programming/telemetry circuitry is believed workable in the context of the present invention. Information may be provided to the cardioverter/pacemaker from the external device and passed to controller 106 via control lines 130. Similarly, information from the card cardioverter/pacemaker may be provided to the telemetry block 120 via control lines 130 and thereafter transferred to the external device.

In one embodiment, the external device 121 is a programmer that may be utilized to diagnose patient conditions and to provide any necessary re-programming functions. In another embodiment, the external device may be a patient interface used to provide information to, and/or receive commands from, the patient. For example, the patient interface may be an externally-worn device such as a wrist band that provides a warning to a patient concerning an impending shock. The patient may be allowed to cancel the shock if the patient believes the shock was prescribed erroneously. This may be accomplished, for example, by pushing a button, or issuing a voice command. The patient interface may provide additional information, including a warning that medical attention is required, and/or an indication concerning a low power source. If desired, the patient interface could automatically place an emergency telephone call via a wireless link, and/or could issue patient positional information via a global positioning system (GPS).

Any other system and method used for the detection and treatment of tachyarrhythmias may be incorporated within the current invention. Such systems and methods are described in U.S. Pat. Nos. 5,849,031, 5,193,535, and 5,224,475. In one embodiment the system may include "tiered therapies" for delivering treatment based on the type of arrhythmia detected by the device. According to this approach, arrhythmias are differentiated by analyzing the rate and morphology of a sensed cardiac signal. Those arrhythmias considered less dangerous such as ventricular tachycardias (VTs) may be treated by delivering a series of low-power, relatively high-rate, pacing pulses to the heart. This therapy is often referred to as anti-tachyarrhythmia pacing therapy (ATP). In contrast, more perilous arrhythmias such as ventricular fibrillations (VFs) may be treated by immediately delivering more aggressive shock therapy. This type of system is described in U.S. Pat. No. 5,193,536, issued to Mehra, U.S. Pat. No. 5,458,619 to Olson, U.S. Pat. No. 6,167,308 to DeGroot, and U.S. Pat. No. 6,178,350 to Olson, et al., all incorporated herein by reference. Within the context of the current invention, ATP therapy is delivered using one or more subcutaneous electrodes in the manner discussed below. In one embodiment of the invention, a separate electrode may be provided within a subcutaneous electrode array for delivering the ATP therapy.

According to another aspect of the inventive system, the device may include means for decreasing discomfort associated with high-voltage shocks. It is well known that high-voltage shocks are painful for the patient. This discomfort can be minimized by decreasing the amount of energy associated with the shock. One mechanism for accomplishing this involves delivering a pre-shock pulse waveform, as described in U.S. Pat. No. 5,366,485 issued to Kroll. In one embodiment, this type of waveform could be a programmable feature that is controlled by controller 106 via parameters stored in RAM 104.

In yet another embodiment of the invention, the implantable device includes a drug pump 10 as shown in FIG. 2. This pump may be used to deliver a biologically-active agent such as an analgesic drug to the patient prior to shock delivery to reduce discomfort. The drug delivery may be accomplished via a catheter 12 that is implanted subcutaneously or within the patient's vascular system. A similar system is described in U.S. Pat. No. 5,893,881 to Elsberry, incorporated herein by reference. Alternatively, or in addition, this pump may deliver an agent such as D-sotalol, Procainamide or Quinidine to reduce the defibrillation threshold of the required shock, thereby serving to reduce pain. In a more complex embodiment, two separate drug pumps might be employed to allow delivery of the threshold reducing agent alone or in conjunction with an analgesic.

Pain control may also be accomplished by providing spinal cord stimulation (SCS). For example, the Medtronic Itrel II implantable neurostimulation system is widely implanted for treatment and alleviation of intractable pain. Clinical reports and studies have shown that SCS can reduce the discomfort associated with high-voltage shocks. This type of system may utilize a lead system of the type described in U.S. Pat. Nos. 5,119,832, 5,255,691 or 5,360,441. These leads, as well as the Medtronic Model 3487A or 3888 leads, include a plurality of spaced apart distal electrodes that are adapted to be placed in the epidural space adjacent to spinal segments T1-T6 to provide SCS stimulation for pain reduction. In this embodiment, initial detection and verification of fibrillation is followed by epidural neural stimulation to produce paraesthesia. Thereafter, a shock may be delivered. Should the cardioversion shock prove unsuccessful, the process is repeated until the cardioversion therapies prove successful or are exhausted. When successful defibrillation is confirmed, the epidural SCS stimulation is halted.

In addition to SCS therapy, other types of stimulation such as Transcutaneous Neurological Stimulators (TENs) may be provided via electrode patches placed on the surface of a patient's body. Subcutaneously-placed electrodes may also be positioned in the T1-T6 area or in other areas of the body to deliver subcutaneous electrical stimulation to reduce pain. In the context of the current invention, the subcutaneously-placed electrode arrays may include specialized electrodes to deliver the subcutaneous stimulation prior to shock delivery to reduce patient discomfort.

Turning now to a more detailed discussion of the electrode systems used with the current invention, the electrode may be of a type shown in FIG. 1. Alternatively, this electrode array may be similar to the Model 6996 SQ commercially-available from the Medtronic Corporation.

FIG. 3A is a top view of an electrode array 300 as may be used with the current invention. Electrode array 300 is coupled to distal end of lead 302. The array includes multiple finger-like structures 304A through 304E. More or fewer of these finger-like structures may be provided. Each finger includes a defibrillation coil electrode shown as 306A through 306E. When connector 308 is coupled to a pulse generator, a cardioversion/defibrillation pulse may be provided via one or more of the electrodes 306A through 306E. In one embodiment, the electrodes that are activated may be selected via a switch provided by the lead.

Electrode array 300 may include one or more sensing electrodes such as electrode 310 provided for sensing cardiac signals. This electrode may be used in a unipolar mode wherein signals are sensed between an electrode and the device housing. Alternatively, sensing may be performed between electrode 310 and one of the coil electrodes 306 or another sensing electrode.

In use, the fingers 304 of electrode array are positioned under the skin on a patient's chest, side, back, or any other point of the body as required. Insulative spacers may be located between the fingers, if desired, to prevent the coil electrodes 306A-E from shorting together. If desired, multiple such electrode arrays may be used in conjunction with the current invention. For example, one electrode array may be positioned on the chest over the left ventricle, while another electrode array is positioned behind the left ventricle on the back. Cardioversion/ defibrillation shocks or pacing pulses may be delivered between the two electrode arrays.

Alternatively, electrical stimulation may be provided between one or more electrode arrays and the device housing. As noted above, sensing of the patient's cardiac signals may be performed between a subcutaneous electrode array and the device can.

FIG. 3B is a top view of an alternative embodiment of electrode array, shown as array 300A. In this embodiment, fingers 320A through 320C have a serpentine shape. More or fewer such fingers may be provided. This shaped array directs current provided by coiled electrodes 322A through 322C through a larger tissue area, thereby decreasing defibrillation thresholds in some instances. This embodiment may also include one or more sensing electrodes 322. Any other shape may be utilized for the electrode array.

The electrodes used with the current invention may be any of the electrode types now known or known in the future for subcutaneous delivery of electrical stimulation. Such electrodes may be coated with a biologically-active agent such as glucocorticolds (e.g. dexamethasone, beclamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory. Such coating may be useful to prevent excessive tissue ingrowth. Such electrodes may further include a low-polarization coating such as TiN. Alternatively, the electrodes may be coated with an antibiotic or other biologically-active agent used to prevent infections and inflammation.

In another embodiment, the can itself may include a subcutaneous electrode array of the type described in U.S. Pat. No. 5,331,966, which is incorporated herein by reference in its entirety. This type of array, which is provided by the Medtronic Model 926 Reveal Plus Implantable Loop Recorder, includes at least two sensing electrodes on the can for sensing of cardiac signals. In all such systems, it will be understood that the electrodes A, B, C on the surface of the housing are electrically isolated from one another and the conductive surface of the pulse generator housing 10 through suitable insulating bands and electrical feedthroughs as described in U.S. Pat. No. 4,310,000, incorporated herein by reference. Examples of possible electrode orientations and configurations of a three electrode system comprising the electrodes are set forth in FIGS. 4A through 4G.

FIG. 4A is a side view of a pulse generator illustrating the orientation of orthogonally-disposed electrodes A, B and C with two electrodes on the connector block 418 and one electrode on the pulse generator case 410. The spacing of the electrodes A, B and C on each of the illustrated orientations of FIG. 4A through 4G may be on the order of about one inch but can be larger or smaller depending on the exact size of the device. Smaller devices and closer spacing will require greater amplification.

FIG. 4B is a side view of a pulse generator wherein at least one of the electrodes extends away from the pulse generator by a lead extension member 420 to achieve a greater inter-electrode spacing, if desirable.

FIG. 4C is a side view of a pulse generator wherein at least one of the electrodes 230 is located at a proximal end of a lead 432, which may be a lead coupled at a distal end to a subcutaneous electrode or electrode array.

FIG. 4D is a side view of a pulse generator wherein multiple electrodes are located of an edge of a device housing. It will be understood that the electrodes placed on the edge of the pulse generator case could constitute insulated pins of feedthroughs extending through the wall of the case. As illustrated in FIGS. 4C and 4D, the relative orientation of the electrodes may vary somewhat from the orthogonal orientation depicted in FIGS. 4A and 4B.

FIG. 4E is a side view of yet another embodiment of a device housing including an array of electrodes.

FIG. 4F is a side view of a device having a first alternative "T" shape. This shape allows at least two of the electrodes A and C to be positioned at a maximum distance from one another, optimizing signal reception between the two electrodes.

FIG. 4G is a side view of a device having a second alternative "boomerang" shape which may be used to optimize electrode positioning so that better signal reception is achieved.

It will be appreciated that the shapes, sizes, and electrode configurations of the devices shown in FIGS. 4A through 4G are exemplary only, and any other shape, size or electrode configuration imaginable is within the scope of the current invention. As will be appreciated by those skilled in the art, those configurations allowing for greater inter-electrode distances will generally provide better signal reception. As such, it is usually desirable to provide electrodes on at least two quadrants of the device.

As described above, in one embodiment, the current invention provides a pulse generator coupled to one or more subcutaneous electrodes or electrode arrays. The electrodes provide electrical stimulation to a patient based on sensed cardiac signals. The sensed signals may be obtained using a selected pair of sensing electrodes, which may reside on one or more of the leads coupled to pulse generator 10, or on the device housing itself, as indicated by FIGS. 4A through 4G.

Although all of the foregoing examples illustrate a housing including three electrodes, more than three electrodes may be provided. In one embodiment, four or more electrodes may be coupled or adjacent to the device, and the physician may select which of the electrodes will be activated for a given patient. In one embodiment, cardiac signals are sensed between a selected pair of the electrodes based on a signal optimization method. One embodiment of this type of method is disclosed in U.S. patent application Ser. No. 09/721,275 filed Nov. 22, 2000 and incorporated herein by reference in its entirety.

Regardless of which one or more electrodes or electrode pairs are selected for monitoring purposes, the sensed cardiac signals may be analyzed to detect the presence of an arrhythmia. The arrhythmia detection system and method could be, for example, that employed by the Medtronic Model 926 Reveal Plus device commercially available from Medtronic Corporation. Alternatively, a detection method such as described in U.S. Pat. Nos. 5,354,316 or 5,730,142 could be employed. If an arrhythmia is detected, appropriate therapy may be administered. As described above, one embodiment of the invention includes at least one subcutaneous defibrillation electrode array. If monitoring indicates the presence of a tachyarrhythmia or ventricular fibrillation, a high-voltage shock may be delivered between one or more subcutaneous defibrillation electrode(s) and a shocking surface of the can, or one or more electrodes on the can. The shock may alternatively be delivered between multiple defibrillation electrodes. The monitoring system would then determine whether the arrhythmia or fibrillation has terminated. If not, another shock will be administered. This therapy will continue until normal rhythm has been restored. In one embodiment, signals indicative of sensed cardiac waveforms may be stored in RAM 104 and later transferred to an external device via a communication system such as telemetry circuitry 120.

According to another aspect of the invention, the sensing electrodes may be placed on a surface of the can that is different from the shocking surface of the can. Preferably, the shocking surface is adjacent to muscle tissue, whereas the sensing electrodes are placed adjacent to subcutaneous tissue.

As described above, therapy for bradyarrhythmia may be provided in addition to, or instead of, the tachyarrhythmia therapy. In this embodiment, output circuit 108 includes the capability to deliver lower-voltage pulses for transthoracic pacing therapy for bradyarrhythmias, as described above in reference to FIG. 1. These lower-voltage pulses could be on the order of between 0 and 10 volts, for example. In one embodiment, these pulses have an amplitude of around 100 volts. Monitoring for a bradyarrhythmia could be accomplished using the sensing electrodes discussed above. For example, the device may be programmed to detect a period of asystole that is greater than a predetermined period, such as three seconds. When a period greater than this length is detected, the output circuit of the device is charged to the pacing voltage. A transthoracic, monophasic pacing pulse may then be delivered between the shocking surface of the can and a subcutaneous electrode or electrode array, or between two such electrode or electrode arrays. The sensing electrodes monitor the cardiac waveform to ensure that the pacing pulse is only delivered during predetermined periods of the cardiac cycle. For example, delivery of the pulse should not occur during the occurrence of a T-wave.

Following delivery of a pacing pulse, the output circuit begins charging in preparation for delivery of another pulse while monitoring of the cardiac signals continues. For example, monitoring of the patient's heart rate may be performed to determine whether it is less than some predetermined rate such as forty beats per minute. If so, another transthoracic, monophasic pacing pulse is delivered. This process of pulse delivery followed by charging of the output circuit is repeated until an intrinsic heart rate of greater than the predetermined minimum rate is detected.

The transthoracic pacing provided by the current invention will likely be uncomfortable for the patient. Thus, this function is not intended to provide chronic therapy. Once therapy delivery has occurred for a bradyarrhythmic episode, a more traditional device should be implanted to provide long-term therapy. In one embodiment, the device may record whether any ACC/AHA class I pacing indications has been met by the detected bradyarrhythmic event. For example, if asystole greater than three seconds and/or an escape rate less than forty beats per minute has been detected, these indications are recorded. This data may then be transferred to an external device to generate a physician notification. Other actions may be taken, such as sounding an alarm, for example.

Figure 5:
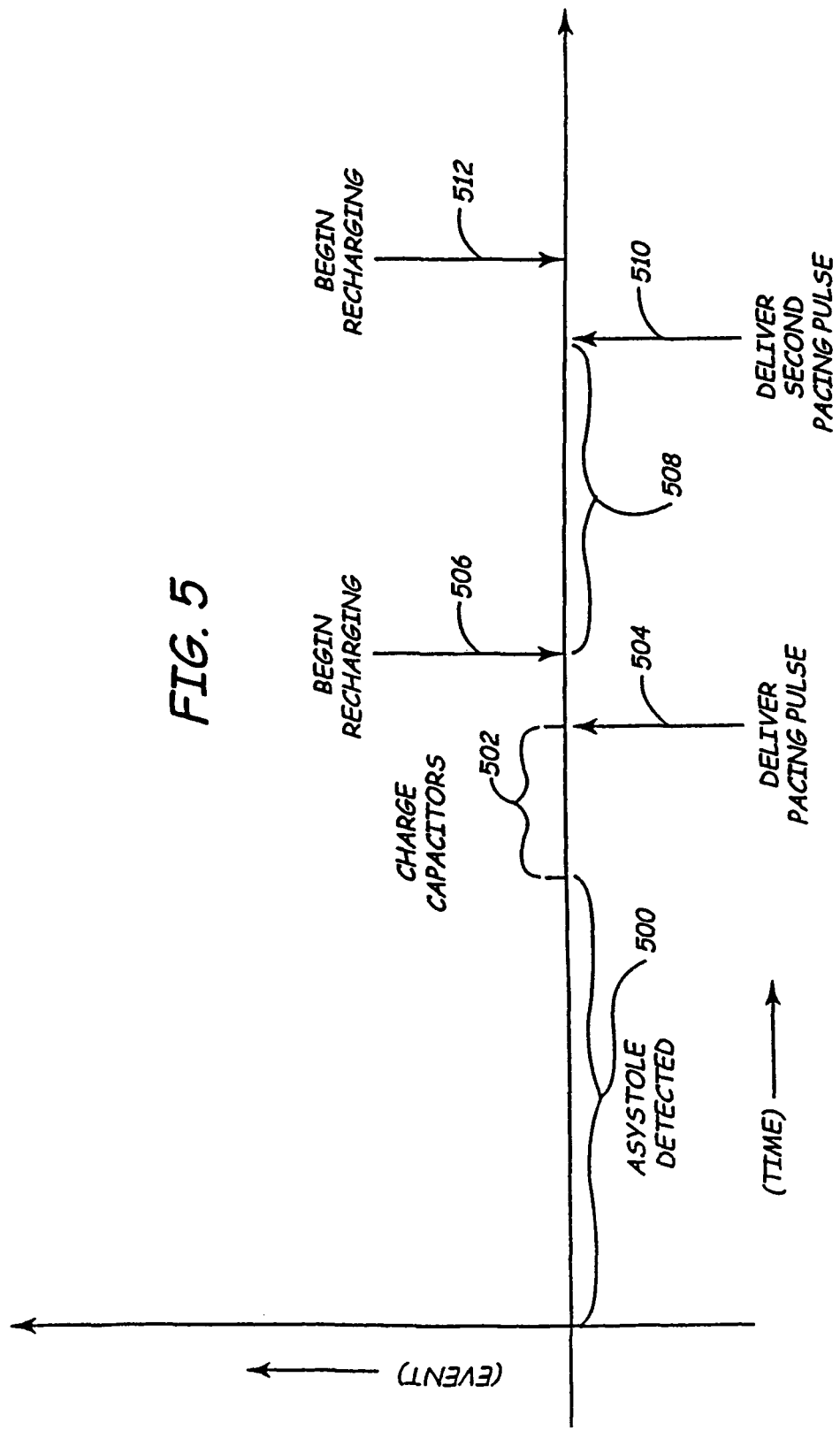
FIG. 5 is a timing diagram illustrating one embodiment of a detection method used during bradyarrhythmia monitoring.

FIG. 5 is a timing diagram illustrating one embodiment of a detection method used during bradyarrhythmia monitoring. If asystole is detected for greater than, or equal to, a first predetermined, time period 500 such as three seconds, charging of output capacitors occurs to a predetermined voltage such as 100 volts. This charging occurs during time period 502. At time 504, a first pacing pulse is delivered, and recharging of the capacitors begins at time 506. Monitoring for an escape rate longer than a predetermined rate occurs during time period 508, which in one embodiment is 100 milliseconds. Thereafter, a second pacing pulse is delivered at time 510 if an intrinsic beat does not occur. At time 512, recharging occurs, and monitoring for the escape rate again proceeds. If such therapy is not discontinued because of the re-occurrence of the patient's intrinsic normal heart beat, the patient will be required to seek immediate emergency attention, since such therapy will be uncomfortable for the patient. The times utilized to provide therapy as shown in FIG. 5 may be programmable.

It may be appreciated from the foregoing discussion that providing repeated therapy, and in particular, repeated high-voltage pacing stimulation, will deplete a system power source, such as a battery, relatively quickly. Therefore, in one embodiment, the power source is rechargeable. For example, the pulse generator may include rechargeable nickel cadmium batteries. Such batteries may be recharged over a period of several hours using a radio frequency link. Alternatively, a rechargeable capacitive energy source such as disclosed in U.S. Pat. No. 4,408,607 to Maurer may be utilized. In yet another embodiment, the pulse generator may include both an implanted radio frequency (RF) receiving unit (receiver) incorporating a back-up rechargeable power supply and a non-rechargeable battery, as described in U.S. Pat. No. 5,733,313 incorporated herein by reference. The rechargeable power supply is charged by an external RF transmitting unit worn by the patient. Any other type of rechargeable power supply known in the art for use with implantable medical devices may be used in the alternative.

In one embodiment, the power source selected for use in the current invention is capable of delivering up to ten therapy shocks, with additional power being available for threshold testing. However, compromises will exist since the power source capacity will determine device size. In yet another embodiment the device is a 75-joule device having a volume of no more than 75 cubic centimeters. Preferably, the device includes a power source and associated charge circuitry that provides a charge time of no more than three minutes during the useful life of the device. In another embodiment, the device should be capable of delivering a 35-joule shock after a one-minute charge time over the useful life of the device.

FIGS. 6 through 9 illustrate various exemplary electrode configurations as may be used with the current invention.

Figure 6:
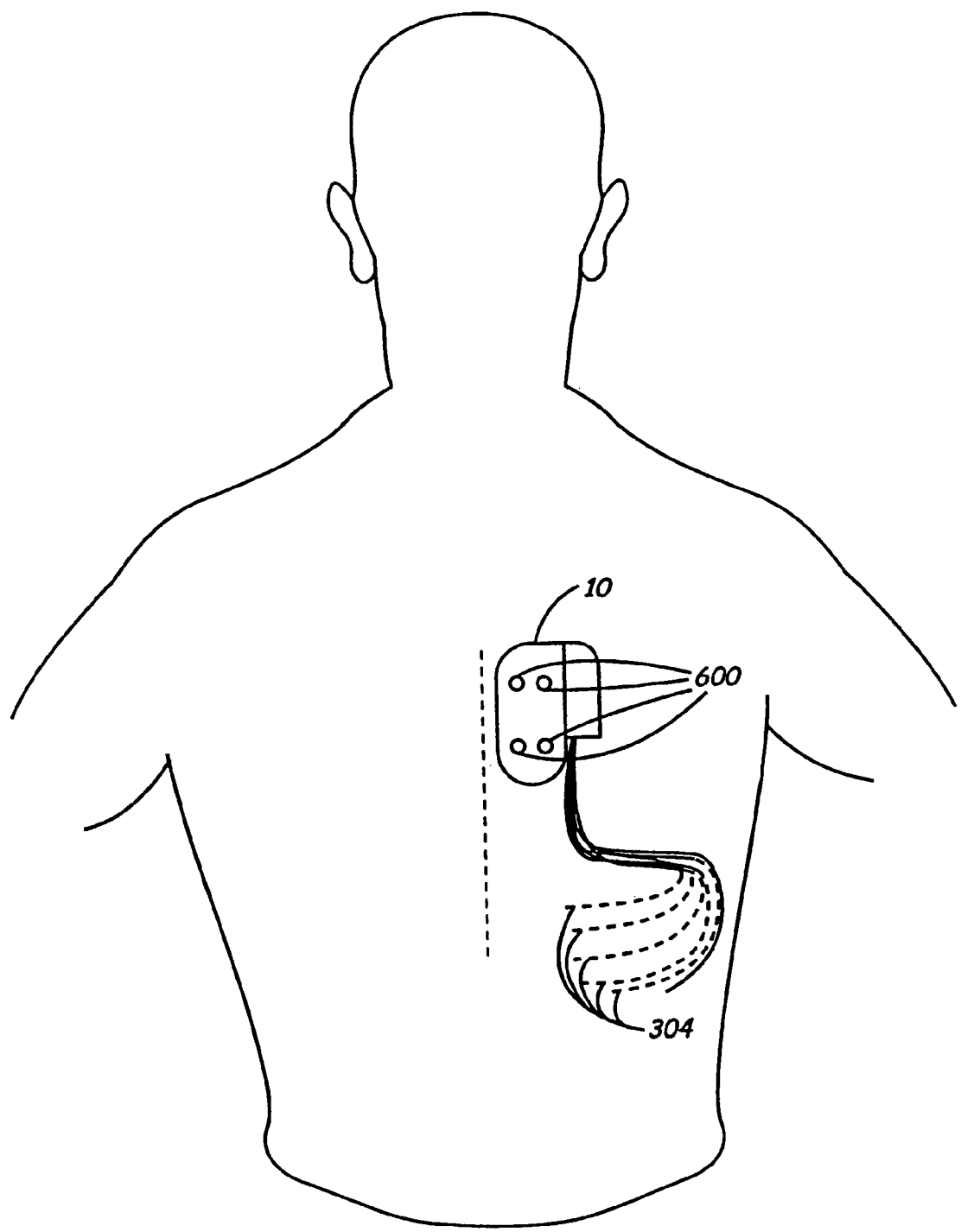
FIG. 6 is a block diagram illustrating an electrode array positioned around a patient's side, with electrode coils extending to the patient's back.

FIG. 6 is a block diagram illustrating an electrode array 300 positioned around a patient's side, with fingers 304 extending to the patient's back. Electrical stimulation is delivered between the electrode array and the device can 10, which is positioned over the left ventricle. In one embodiment, sensing electrodes 600 are positioned substantially facing toward subcutaneous tissue.

Figure 7:
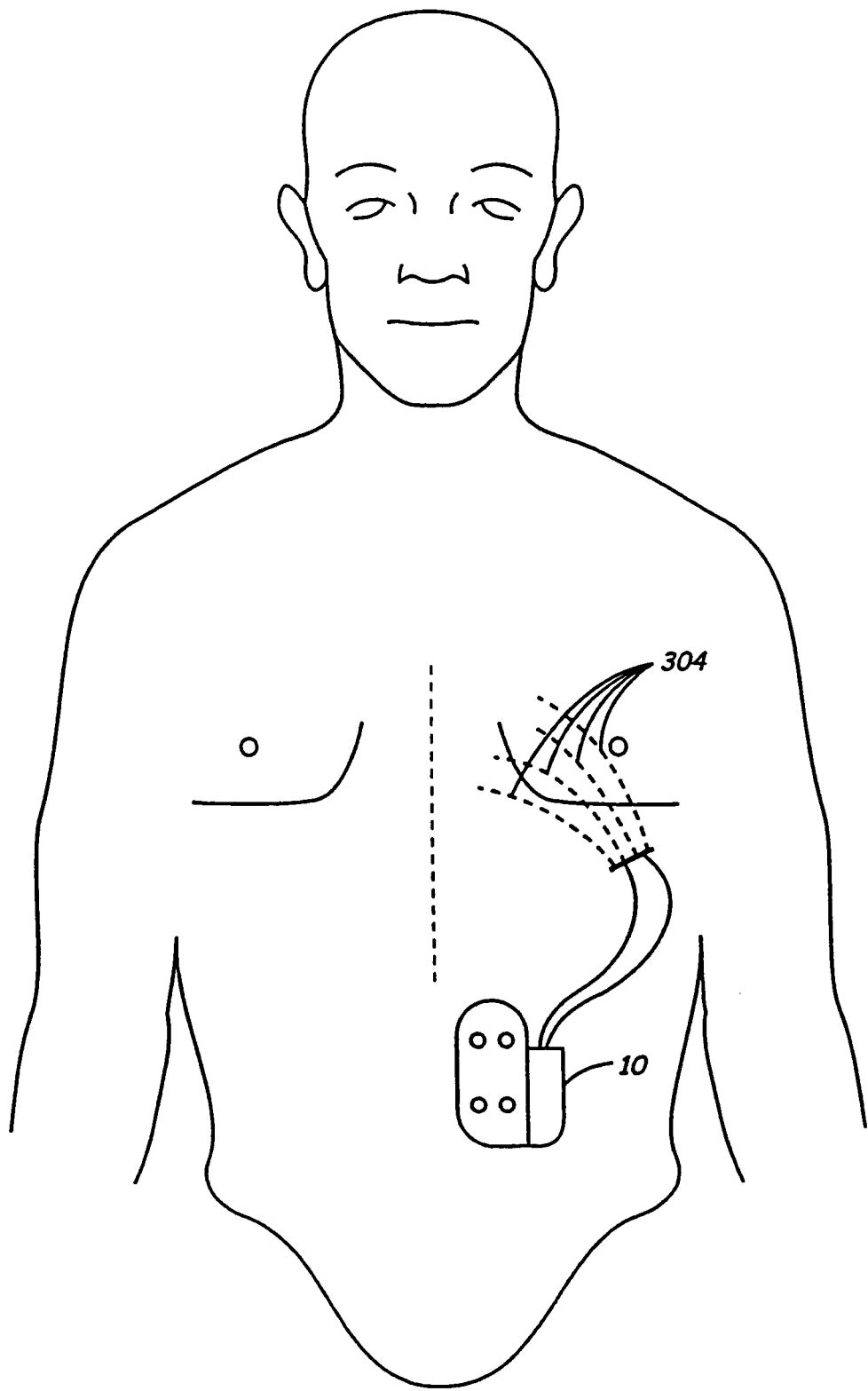
FIG. 7 is a block diagram illustrating an electrode array positioned on patient's back in a more superior position.

FIG. 7 is a block diagram illustrating an electrode array positioned on a patient's back in a more superior position than is shown in FIG. 6. Electrical stimulation is delivered between the electrode army and the device can 10, which is positioned in the abdominal cavity.

Figure 8:
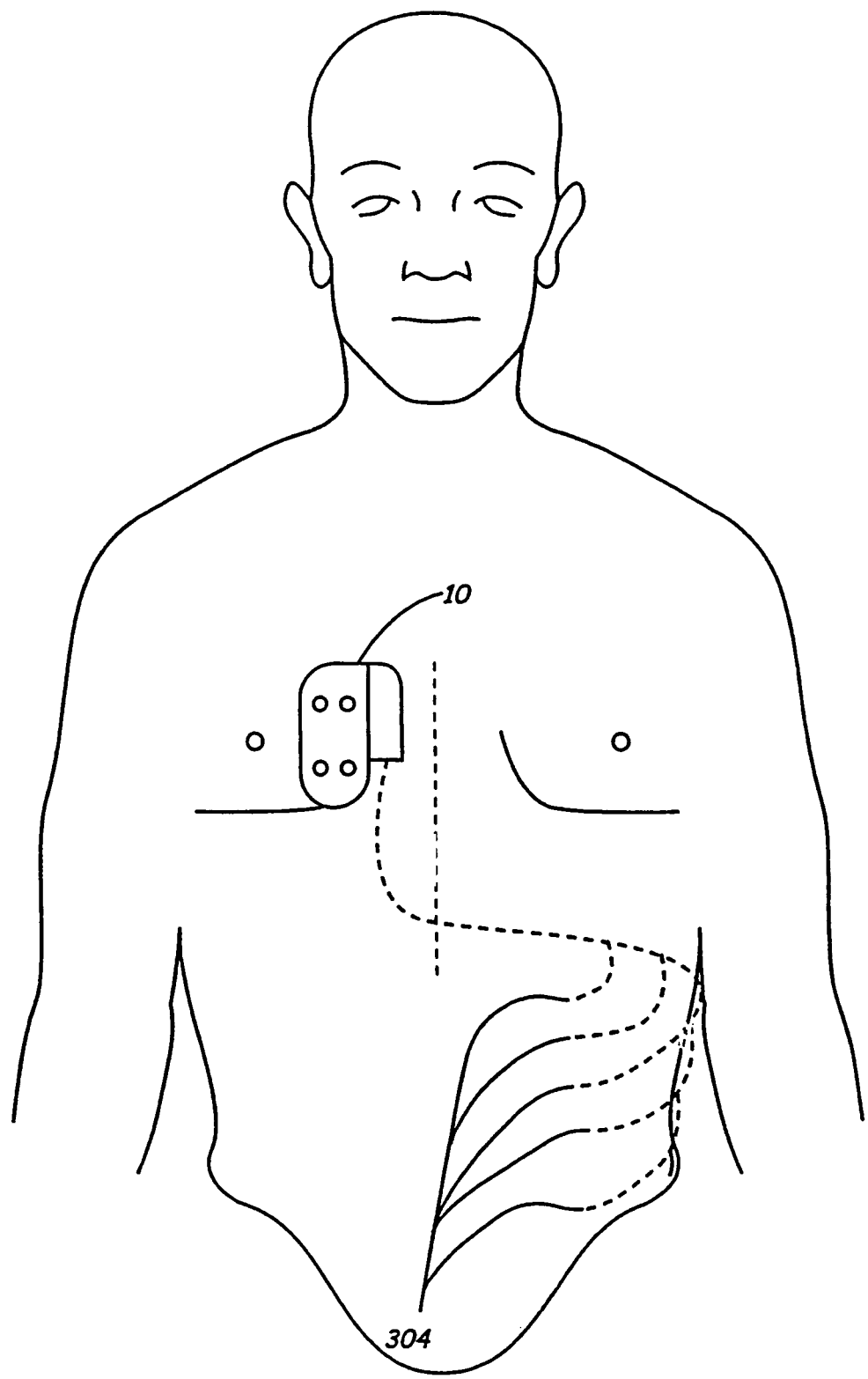
FIG. 8 is a block diagram illustrating an electrode array positioned around a patient's side, with coil electrodes extending to the patient's back in a more posterior position.

FIG. 8 is a block diagram illustrating an electrode array positioned around a patient's side, with fingers 304 extending to the patient's back in a more posterior position than is shown in FIGS. 6 or 7. Electrical stimulation is delivered between the electrode array and the device can, which is positioned proximal the right-side of the heart.

Figure 9:
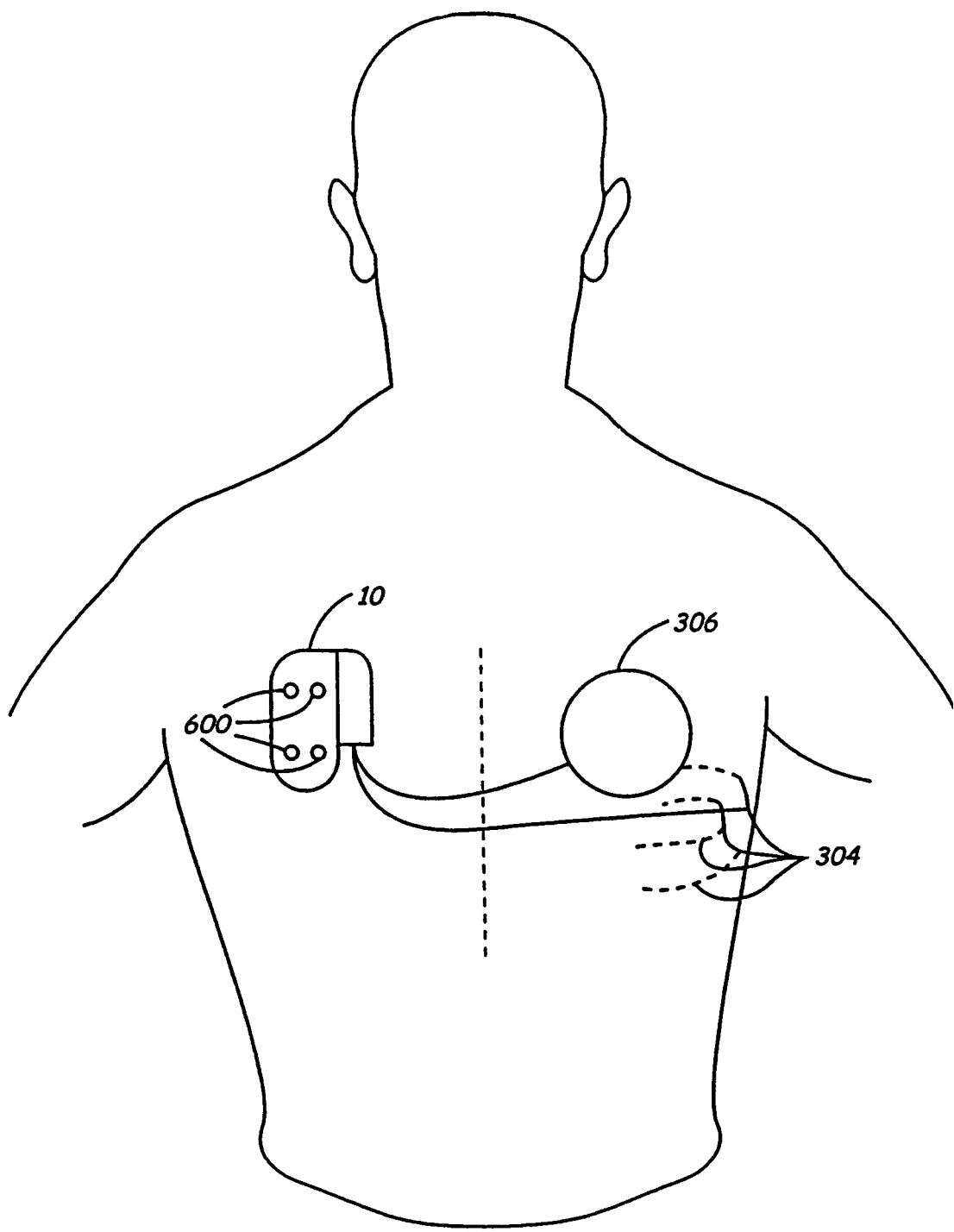
FIG. 9 is a block diagram illustrating an electrode array positioned on a patient's back, and a second subcutaneous disk electrode positioned on a patient's chest.

FIG. 9 is a block diagram illustrating an electrode array with fingers 304 positioned on a patient's back, and a second subcutaneous disk electrode 306 such as electrode 16 (FIG. 1) positioned in a patient's chest. Electrical stimulation may be delivered from one of electrodes 304 or 306 to another electrode and/or the device housing 10. Alternatively, stimulation may be provided from both electrode assemblies to the device housing. In yet another embodiment, one or more additional subcutaneous electrode or electrode arrays may be coupled to the device for providing high-voltage shocks, for sensing cardiac signals, and/or for delivering SCS, TENs, or subcutaneous low-voltage stimulation as discussed above. If desired, the device may include programmable logic to selectably enable those electrode and/or electrode arrays to be activated during a given therapy delivery session. For example, switching networks may be incorporated into output circuitry 108 and/or input circuitry 110 (FIG. 2) such that this type of programmably selected therapy may be provided. In one instance, it may be desirable to activate one electrode configuration to optimize sensing of cardiac signals, while utilizing another configuration to provide optimal therapy delivery.

The above-described inventive system and method provides a therapy that avoids the risks of transvenous lead delivery. Such a system may be used for patients that are at-risk for arrhythmias, but have not yet experienced a confirmed arrhythmic episode. The device may therefore provide a needed long-term monitoring function, as well as any interventional therapy that is required. Preferably, after an episode is detected and therapy is delivered for a first time, the current system would be replaced with a more conventional implantable defibrillator.

As discussed above, the inventive system provides many important benefits over other conventional systems for some patients. The procedure is faster because there is no need for venous or epicardial access, and therefore the procedure is less invasive, and would not require procedures needing sophisticated surgical facilities and devices. Additionally, the implant procedure can be accomplished without exposing the patient to potentially-harmful radiation that accompanies fluoroscopy. The risk of infection is reduced, and the procedure may be provided to patients that are contraindicated for a more traditional device. Additionally, one hundred percent patient compliance is achieved, and the system is more comfortable than externally-worn devices. The system is well suited for pediatric use, since the placement of the electrodes allows lead length to be easily extended as a patient grows. The system may also be employed in parts of the world where more long-term therapies and treatments are not available, and where sophisticated surgical skills and equipment cannot be readily obtained.

The invention claimed is:

1. A system for providing arrhythmia therapy to a patient comprising:
    an implantable pulse generator having a device housing, wherein a portion of the device housing is configured to function as an electrode;
    a sensing circuit positioned within the device housing and coupled to the implantable pulse generator;
    a subcutaneous electrode array comprising at least three discrete electrode supporting fingers, wherein the fingers support a plurality of subcutaneous electrodes coupled to the implantable pulse generator to deliver electrical stimulation to the patient between one or more of the plurality of electrodes of the subcutaneous electrode array and the portion of the device housing, upon detection by the sensing circuit of an arrhythmia,
    a single lead, wherein the at least three discrete electrode supporting fingers are coupled to the implantable pulse generator by the single lead, and each of the plurality of electrodes of the subcutaneous electrode array is separately activatable to deliver the electrical stimulation; and
    a switch provided by the lead, the switch being configured to select which one or more of the plurality of electrodes of the subcutaneous electrode array are activated to deliver the electrical stimulation.

2. The system of claim 1, wherein the subcutaneous electrode array is a defibrillation electrode array to deliver relatively high-voltage electrical stimulation to the patient.

3. The system of claim 2, wherein the sensing circuit utilizes the defibrillation electrode array and the device housing to sense for an arrhythmia.

4. The system of claim 1, wherein the sensing circuit includes at least two sensing electrodes on at least a first surface of the device housing to sense cardiac signals.

5. The system of claim 4, wherein the device housing includes at least one surface to deliver high-voltage shocks, and wherein the surface to deliver high-voltage shocks is different from the at least first surface of the device housing.

6. The system of claim 1, wherein the device housing includes at least one surface to deliver high-voltage shocks.

7. The system of claim 1, wherein at least one of the discrete electrode supporting fingers further supports a sensing electrode coupled to the sensing circuit.

8. The system of claim 7, wherein the sensing circuit is configured to sense a signal between the sensing electrode and the device housing.

9. The system of claim 7, wherein the sensing circuit is configured to sense a signal between the sensing electrode and a selected electrode of the subcutaneous electrode array.

10. The system of claim 1, wherein at least one of the three discrete electrode supporting fingers extends along a longitudinal axis, and includes a first bend extending in a first lateral direction away from the longitudinal axis, and a second bend extending in a second lateral direction away from the longitudinal axis, wherein the first and second lateral directions are opposite of each other.

11. The system of claim 10, wherein the second bend is distal to the first bend along the longitudinal axis.

12. The system of claim 11, wherein the at least one electrode supporting finger further includes a third bend extending in the first lateral direction, the third bend being distal to the second bend.

13. The system of claim 12, wherein the at least one electrode supporting finger further includes a fourth bend extending in the second lateral direction, the fourth bend being distal to the third bend.

14. The system of claim 13, wherein the at least one electrode supporting finger includes one of the plurality of subcutaneous electrodes along its respective third and fourth bends.

15. The system of claim 14, wherein the at least one electrode supporting finger includes a fifth bend extending in the first lateral direction, the fifth bend being distal to the fourth bend.

16. The system of claim 15, wherein the fifth bend includes a sensing electrode.

17. The system of claim 14, wherein the plurality of subcutaneous electrodes are coiled electrodes.

18. The system of claim 12, wherein the longitudinal axis and each of the first, second, and third bends are disposed in a single plane.

* * * * *